(12) United States Patent
Matthew et al.

(10) Patent No.: US 6,313,089 B1
(45) Date of Patent: *Nov. 6, 2001

(54) COMPLEXES OF APOLIPOPROTEIN E AND CILIARY NEUROTROPHIC FACTOR (CNTF) AND METHODS OF USE

(75) Inventors: William D. Matthew; Warren J. Strittmatter; Catherine R. Gutman, all of Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/135,905

(22) Filed: Aug. 18, 1998

Related U.S. Application Data (60) Provisional application No. 60/056,605, filed on Aug. 20, 1997.

(51) Int. Cl.[7] .................. A61K 38/18; C07K 14/475; C07K 14/775
(52) U.S. Cl. ............... 514/2; 514/21; 530/350; 530/399; 424/185.1; 424/195.11
(58) Field of Search .................. 530/399, 350; 514/2, 21; 424/185.1, 195.11

(56) References Cited

U.S. PATENT DOCUMENTS

| 5,364,769 | 11/1994 | Rosenthal | 435/69.1 |
| 5,508,167 | * 4/1996 | Roses et al. | 435/6 |
| 5,604,202 | 2/1997 | Kessler et al. | 514/12 |

FOREIGN PATENT DOCUMENTS

| 0731108 | 9/1996 | (EP) . |
| WO 85/00974 | 3/1985 | (WO) . |
| WO 91/04316 | 4/1991 | (WO) . |
| WO 95/05845 | 3/1995 | (WO) . |
| WO 95/06456 | 3/1995 | (WO) . |
| WO 95/22342 | 8/1995 | (WO) . |

OTHER PUBLICATIONS

Ngo et al., 'Computational Complexity , Potein Structure Prediction, And the Levinthal Paradox,' The Protein Folding Problem and Tertiary Structuer Prediction. Ed. K. Merz and L. Le Grand. BirkHauser, Boston MA. pp. 491–495, 1994.*

Yuen et al. 'Therapeutic Potential Of Neurotrophic Factors For Neurological Disorders', Annals Neurology, vol. 40 No. 3, pp 346–354, Sep. 1996.*

Hefti, Franz. 'Nerothrophic Factor Therapy For Nervous System Degerative Diseases', Journal of Neurobiology, vol. 25, 11, pp. 1418–1435, 1994.*

Abstract: 'Apolipoprotein E3 Binds To And Potentiates Teh Biologic Activity Of Ciliary Neurotrophic Factor'; Annual Meeting of the Society for Nuroscience, Nov. 16–21, 1996, Nov. 1996.*

Gutman et al., 'Apoliporotein E Binds To And Potentiates The Biological Activity Of Ciliary Neurotrophic Factor', The Journal of Neuroscience, vol. 17, No. 6, pp. 6114–6121, Jul. 1997.*

Co–pending U.S. Application No. 09/162,072, filed Sep. 28, 1998 (priority from Provisional Application No. 60/060,533, filed Sep. 30, 1997).

International Search Report, Int'l. Filing Date: Aug. 19, 1998, Atty. Docket No.: 5405/124WO.

Gutman et al.; "Apolipoprotein E Binds to and Potentiates the Biological Activity of Ciliary Neurotrophic Factor"; *The J. of Neuroscience*, 17(16):6114–6121, Aug. 1997.

Abstract: "Apolipoprotein E3 Binds to and Potentiates the Biologic Activity of Ciliary Neurotrophic Factor"; *Annual Meeting of the Society for Neuroscience*, Nov. 16–21, 1996.

Gutman et al., Apolipoprotein E Binds to and Potentiates the Biology Activity of Ciliary Neurotrophic Factor, The Journal of Neuroscience, 17(16):6114–6121, Aig. 1997.

Holtzman et al., Low Density Lipoprotein Receptor–Related Protein Mediates Apolipoprotein E–Dependent Neurite Outgrowth in a Central Nervous System–Derived Neuronal Cell Line, Proc, Natl. Acad. Sci. USA, 92:(9480–9484) Oct. 1995.

* cited by examiner

Primary Examiner—Christopher S. F. Low
Assistant Examiner—Anish Gupta
(74) Attorney, Agent, or Firm—Myers Bigel Sibley & Sajovec, P.A.

(57) ABSTRACT

Provided herein are compositions comprising complexes of apolipoprotein E and ciliary neurotrophic factor. The apolipoprotein E can be any isoform, but is preferably apolipoprotein E3. Also preferred are covalent complexes of apolipoprotein E and ciliary neurotrophic factor, more preferably those formed by intermolecular disulfide bonds between cysteine residues. Further provided are methods of enhancing the survival of neural cells by administering a composition comprising a complex of apolipoprotein E and ciliary neurotrophic factor. The claimed methods can be carried out both in vitro and in vivo.

27 Claims, 1 Drawing Sheet

*FIG. 1.*

COMPLEXES OF APOLIPOPROTEIN E AND CILIARY NEUROTROPHIC FACTOR (CNTF) AND METHODS OF USE

RELATED APPLICATION INFORMATION

This application claims the benefit of U.S. Provisional Application No. 60/056,605 filed Aug. 20, 1997, which is hereby incorporated by reference.

STATEMENT OF FEDERAL SUPPORT

This invention was made with Government support under grant number R01 AG12532-01 from the National Institutes of Health. The Government has certain rights in this invention.

FIELD OF THE INVENTION

The present invention relates to compositions comprising complexes of apolipoprotein E and ciliary neurotrophic factor, and methods of administering the same.

BACKGROUND OF THE INVENTION

Apolipoprotein E (protein: apoE; allele: APOE) is the principal apolipoprotein in the brain (for review, see Mahley, (1988) Science 240, 622) and cerebrospinal fluid (CSF) (Pitas et al., (1987) J. Biol. Chem. 262, 14352). Several observations have implicated a role for apoE in the injured nervous system. Expression of apoE mRNA by astrocytes in the hippocampus increases following entorhinal cortex lesion (Poirier et al., (1991) Mol. Brain Res. 11, 97). Oligodendrocytes and macrophages increase expression of apoE following optic and sciatic nerve injury, respectively (optic: Stoll et al., (1989) GLIA 2, 170; sciatic: Skene and Shooter, (1983) Proc. Nat. Acad. Sci. USA 80, 4169; Stoll and Mueller, (1986) Neurosci. Lett. 72, 233), and apoE protein accumulates to 5% of total extracellular protein following peripheral nervous system (PNS) injury (Skene and Shooter, (1983) Proc. Nat. Acad. Sci. USA 80, 4169). APOE is a susceptibility gene for familial and late-onset Alzheimer's disease (AD: Strittmatter et al., (1993) Proc. Nat. Acad. Sci. USA 90, 1977; for review see Strittmatter and Roses, (1995) Proc. Nat. Acad. Sci. USA 92, 4725). The gene dose of APOE4, one of the three major alleles of APOE in humans, is correlated with increased risk and decreased average age of onset of AD. These observations suggest a role for apoE in the injured or diseased nervous system.

Three major isoforms of apoE in humans—apoE2, apoE3 and apoE4—are distinguished by cysteine-arginine substitutions at positions 112 and 158. The most common isoform, apoE3, is secreted as a 299 amino acid protein with a single cysteine at position 112 and an arginine at position 158; apoE2 contains a cysteine at position 158 and apoE4 contains an arginine at position 112. ApoE contains two distinct structural and functional domains, a hydrophobic domain and a hydrophilic receptor binding domain (Weisgraber, (1994) Adv. Prot. Chem. 45, 249). The crystal structure of the hydrophilic domain of apoE is homologous to the family of four-helix bundle growth factors, including ciliary neurotrophic factor, although the sequences of these proteins diverge greatly. CNTF; reviewed by Bazan, (1991) Neuron 7, 197; Mott and Campbell, (1995) Curr. Opin. Struc. Biol. 5, 114; apoE crystal structure by Wilson et al., (1991) Science 252, 1817; CNTF crystal structure by McDonald et al., (1995) EMBO J. 14, 2689.

The cellular expression pattern of CNTF parallels that of apoE. CNTF expression in astrocytes is upregulated near sites of injury in the CNS (Ip et al., (1993) Eur. J. Neurosci. 5, 25) and myelinating Schwann cells in the PNS contain high levels of cytoplasmic CNTF (Rende, et al., (1992) GLIA 5, 25) that is released following nerve injury. CNTF immunoreactivity and biologic activity in peripheral nerve are detectable extracellularly for 7 days following PNS injury (Sendtner et al., (1992) J. Cell Biol. 118, 139). CNTF exerts a broad range of biological activities, many of which suggest that CNTF acts as an injury-associated survival factor in the nervous system (reviewed by Adler, (1993) Curr. Opin. Neurobio. 3, 785). In vivo, CNTF supports the survival of intermediolateral column spinal cord neurons after adrenal medulla lesion (Blottner et al., (1989) Neurosci. Let. 105, 316), reduces the axotomy-induced death of facial nucleus neurons (Sendtner et al., (1990) Nature 345, 440) and potentiates peripheral nerve regeneration (Sahenk et al., (1994) Brain Res. 655, 246). In vitro, CNTF promotes the survival of many neuronal cell types, including: sensory and sympathetic ganglion neurons of the PNS (sensory: Skaper and Varon, (1986) Brain Res. 389, 39; sympathetic: Saadat et al., (1989) J. Cell Biol. 108, 1807; cerebellar neurons: Larkfors et al., (1994) Eur. J. Neurosci. 6, 1015; and embryonic hippocampal neurons: Ip et al., (1991) J. Neurosci. 11, 3124).

CNTF has been used in vivo to protect striatal neurons in an animal model of Huntington's disease (Anderson et al., (1996) Proc. Nat. Acad. Sci. USA 93, 7346). In this study, CNTF, but not BDNF, NGF or NT3, afforded protection against intrastriatal injection of the excitotoxin quinolinic acid. The best studied in vivo system for CNTF function is the peripheral nerve. Following unilateral transection of the sciatic nerve in postnatal day 5 mice there is a 66% loss of motoneurons (Kashihara et al., (1987) J. Physiol. (London) 386, 135; Snider et al., (1992) J. Neurobiol. 23, 1231) and a 33% loss of sensory neurons (Lo et al., (1995) Exp. Neurol. 134, 49) 10 days postsurgery. Local delivery of CNTF to the transection site rescues axotomized motor (Li et al., (1994) J. Neurobiol. 25, 759) and sensory neurons (Lo et al., (1995) Exp. Neurol. 134, 49). When the sciatic nerves of postnatal day 10 or adult mice are transected, no neuronal death is detected. One interpretation of these experiments is that Schwann cell derived CNTF is a survival factor for axotomized motor and sensory neurons. Because CNTF production by Schwann cells in the sciatic nerve increases dramatically over the first three weeks of postnatal development, the first postnatal week provides a window of time when Schwann cell derived CNTF is limited and survival after axotomy is partial.

Given that CNTF supports the growth, differentiation and survival of a wide variety of neuronal cell types, CNTF is an important candidate as a neuronal survival and regeneration factor following injury. Accordingly, there is a need in the art for strategies of potentiating the activity of CNTF to slow the progression of neurodegenerative diseases, to protect against neural degeneration after injury, and to facilitate nerve regeneration.

SUMMARY OF THE INVENTION

Disclosed herein is the novel discovery that apoE binds to and potentiates the biological actions of the neurotrophic factor CNTF.

As a first aspect, the present invention provides a composition comprising a complex of apolipoprotein E (apoE) and ciliary neurotrophic factor (CNTF). The apoE component can be apoE2, apoE3, or apoE4, and can be in a lipid-bound or delipidated state. Furthermore, the complex can be formed by either covalent or noncovalent interactions between the apoE and CNTF molecules.

As a second aspect, the present invention provides a method of enhancing the survival of neural cells, comprising administering to the neural cells a survival-enhancing amount of a composition comprising a complex of apolipoprotein E and ciliary neurotrophic factor. The claimed methods can be carried out both in vitro and in vivo.

As a third aspect, the present invention provides a method of administering a composition comprising a complex of apolipoprotein E and ciliary neurotrophic factor in a therapeutically-effective amount to a subject in need thereof.

These and other aspects of the invention are set forth in more detail in the description of the invention below.

DETAILED DESCRIPTION OF THE INVENTION

The nervous system responds to acute injury and to chronic neurodegenerative diseases by the coordinated expression of many proteins, including growth and survival factors, cell surface receptors, and secreted extracellular proteins. Many of these proteins, most notably the neurotrophic factors, play a role in recovery from injury and protection from neurodegenerative disease. Within the complex milieu of the traumatized nervous system it is extremely unlikely that any one growth factor functions alone. Cooperative interactions of growth factors with other proteins are likely to play important roles in the stability, localization or presentation of growth factors. Optimal functioning of growth and survival factors released at sites of injury is critical for recovery from neural trauma. In both the peripheral and central nervous systems the expression of apoE is increased in acute and chronic stress.

Disclosed herein is the discovery that apoE binds to and enhances the activity of CNTF, a neurotrophic factor that promotes the survival of sensory, sympathetic, hippocampal, cerebellar and motor neurons. While not wishing to be held to any particular theory, the finding that apoE binds to CNTF suggests that apoE may act as an accessory protein for this growth factor, regulating its metabolism or biological activities. One mechanism might be the localization of CNTF to extracellular matrix by tethering it through an apoE molecule. CNTF immunoreactivity is localized to the extracellular matrix of peripheral nerve following injury. It has previously been shown that apoE binds to the extracellular matrix protein laminin, and thereby increases neuron adhesion, and alters growth cone spreading (Huang et al., (1995) *Exp. Neurology* 136, 251). ApoE may additionally or alternatively alter the biological activity of the bound growth factor by other mechanisms, such as inhibiting its proteolytic inactivation, or by altering its ability to interact with its cell-surface receptor. Interactions between apoE and CNTF may be important in modulating the role of CNTF in neural regeneration responses, both in acute and in chronic disorders of the nervous system.

Disclosed herein are compositions containing apoE:CNTF complexes. The interaction of ApoE and CNTF to form a complex potentiates the neurotrophic actions of CNTF. The claimed complexes can be formed by simply mixing ApoE and CNTF (typically aqueous solutions) together. Those skilled in the art will appreciate that compositions containing apoE:CNTF complexes produced in this manner will generally include ApoE and CNTF monomers, homodimers, homotrimers, etc., as well. In general, 15% to 60%, more preferably 20% to 50%, more preferably 25% to 40% of the ApoE and CNTF molecules will be found in apoE:CNTF complexes. The term "apoE:CNTF complex" as used herein encompasses apoE:CNTF complexes containing monomers, dimers, trimers, and larger multimers of CNTF. Complexes of apoE:CNTF also includes complexes of apoE monomers, homodimers, homotrimers, etc. with CNTF monomers, homodimers, homotrimers, etc. Thus, the present invention encompasses complexes between one or more ApoE monomers with one or more CNTF monomers. Heterodimeric apoE:CNTF complexes and heterotrimeric apoE:(CNTF)$_2$ complexes are preferred. Those skilled in the art will appreciate that apoE:CNTF complexes may also be more loosely associated with additional molecules (which may be additional apoE or CNTF molecules).

Alternatively, apoE may first be bound to a substrate, such as a plastic surface, prior to being exposed to and forming a complex with CNTF. As a further alternative, the apoE:CNTF complex can be bound to a substrate after complex formation.

The strength of the binding interaction between apoE and CNTF is high; with a dissociation constant of the claimed apoE:CNTF complexes of at least $10^{-7}$, preferably at least $10^{-8}$, more preferably at least $10^{-9}$. Complexes can be formed by both covalent and noncovalent interactions, with covalent complexes of apoE and CNTF being preferred, and complexes formed by intermolecular disulfide bonds between cysteine residues being most preferred. Also preferred are covalent complexes formed between apoE3 and CNTF. Typically, covalent apoE:CNTF complexes are stable in a solution containing at least 1% SDS.

The only difference in primary structure between apoE3 and apoE4 is a cysteine and arginine substitution at position 112 (apoE3 has only one cysteine, apoE4 has none). It is possible that apoE3 has a functional biologic advantage over apoE4 because it forms a disulfide bond with the one cysteine in CNTF. Once formed, a disulfide bond is very stable; considerably more stable than ionic interactions. Therefore, the interaction between apoE3 and CNTF may be particularly stable as a result of disulfide bond formation. It is likely that this higher avidity binding gives apoE3 an advantage over apoE4 in promoting CNTF function under certain circumstances in vivo.

The apoE component of the claimed complexes can be apoE2, apoE3, apoE4 or a combination thereof. Preferably, the complexes contain apoE3. ApoE variants and fragments that bind to the apoE receptor and/or complex with and potentiate the biological actions of CNTF are also encompassed by the present invention. ApoE can be from any species of origin, preferably of mammalian origin, more preferably human origin. The apoE molecules can be in a lipidated or delipidated state, with delipidated being preferred.

ApoE can be purified from natural sources (i.e., blood, serum or peritoneal fluid). Co-pending U.S. Application Ser. No. 08/539,328 describes the isolation of native apoE from peritoneal fluid, the disclosure of which is incorporated herein in its entirety by reference. The majority of apoE from sera is associated with lipoprotein particles. Purification of apoE from sera requires delipidation with organic solvents or detergents, which causes significant protein denaturation. Lipoprotein isolation by ultra centrifugation, with subsequent lyophilization and delipidation of lipoproteins, and chromatographic isolation of apoE, is described in Rall et al., (1986) *E. Methods Enymol.* 128, 273. An alternative method for isolation of apoE from a mixture of apolipoproteins utilizes gel electrophoresis. Purification of apoE isoforms may be accomplished using isoelectric focusing techniques (Rall et al., (1986) *E. Methods Enzymol.* 128, 273).

ApoE may also be separated from contaminating proteins using heparin-sepharose chromatography, which utilizes the heparin-binding property of apoE. Rall et al., (1986) *E. Methods Enzymol.* 128, 273. ApoE may be isolated and/or purified, optionally to homogeneity by conventional techniques such as affinity chromatography, size-exclusion chromatography, gas chromatography, HPLC, and combinations thereof. Separation of the non-cysteine containing E4 isoform of apoE from contaminating cysteine-containing proteins may be accomplished using thiopropyl chromatography on thiopropyl Sepharose (Weisgraber et al. (1983), *J. Biol. Chem.* 258, 2508).

Recombinant apoE can be produced using methods known in the art, and human recombinant apoE is commercially available. However, recombinant protein is not in the native glycosylated form and is subject to denaturation and oxidation during purification.

The CNTF component of the complex can also be from a native or recombinant source, and can be produced by any means known in the art. See, e.g., Stockli et al., (1989) *Nature* 342, 920; U.S. Pat. No. 5,141,856 to Collins et al.; Manthorpe et al., (1986) *Brain Res.* 367, 282; and EP No. 0 385 060. Moreover, the CNTF component of the claimed apoE:CNTF complexes can be from any species of origin, preferably of mammalian origin, more preferably of human origin. Also claimed are complexes containing CNTF variants, such as R63 human CNTF, disclosed in U.S. Pat. No. 5,349,056 to Panayotatos, in which the glutamine in position 63 of human CNTF is replaced with arginine. CNTF fragments that bind to CNTF receptors and/or elicit the neurotrophic actions of CNTF are also encompassed by the present invention. For example, U.S. Pat. No. 5,593,857 to Higaki et al. and WO 9303758 to Cordell et al. describe truncated human CNTF lacking the C-terminal portion, which retains full biological activity as compared with full-length CNTF.

Methods of enhancing the survival of neural cells by administration of an apoE:CNTF complex are also an aspect of the present invention. The term "enhancing the survival" of neural cells is intended to be construed broadly, and includes neurotrophic and neuro-regenerative actions of the claimed compositions. Alternatively, the expression "enhancing the survival" of neural cells refers to the action of the claimed compositions in protecting neural cells from injury and/or improving recovery from neural injury. "Neural cells" includes the cells and tissues of the central nervous system and the peripheral nervous system, both in vitro and in vivo. Compositions comprising apoE:CNTF complexes for use in the claimed methods are as described in more detail hereinabove.

ApoE:CNTF complexes can be administered to neural cells in vitro. Typically, in vitro administration will simply require adding a solution (i.e., aqueous) containing the apoE:CNTF complexes to the culture medium. Alternatively, the apoE and CNTF components can be added individually, either concurrently or sequentially, to the culture medium. As a further alternative, the apoE molecule or the apoE:CNTF complex can be bound to a substrate (i.e., a tissue culture dish or petri dish), preferably prior to culturing cells on the substrate. It is well-known in the art that apoE binds to plastic or coated (i.e., with extracellular matrix proteins such as laminin) surfaces of tissue culture plates.

Complexes of apoE and CNTF, which potentiate the activity of CNTF, are useful in vitro for culturing neural cells, such as embryonic chick ciliary ganglion neurons. U.S. Pat. No. 5,349,056 to Panayotatos; Manthorpe et al. (1980), *J. Neurochem.*, 34, 69. As established by U.S. Pat. No. 5,349,056 to Panayotatos and U.S. Pat. No. 5,332,672 to Conover et al., CNTF molecules with enhanced activity find use in promoting differentiation, proliferation or survival in vitro of cells that are responsive to CNTF, including cells that express receptors of the CNTF/IL-6/LIF receptor family, or any cells that express the appropriate signal transducing component, as described, for example, in Davis et al. (1992), *Cell* 69, 1121.

The claimed apoE:CNTF complexes also find use in tissue culture, because the rate of proteolytic degradation of the complexed CNTF is greatly reduced.

The claimed complexes also find use in methods of quantifying or purifying CNTF receptors, anti-CNTF antibodies, or other proteins that bind CNTF. ApoE is readily bound to plastic surfaces, such as test tubes and microtiter plates. Thus, CNTF can be tethered to plastic surfaces for use in sandwich assays or affinity purification techniques, which are well-known to those skilled in the art.

The claimed apoE:CNTF complexes can also be administered to a subject in vivo. Methods of administration and pharmaceutical formulations of the claimed compositions are described in more detail hereinbelow. The methods of the invention are useful for treating a subject afflicted with a neurodegenerative disease and subjects who have experienced injury or trauma to neural tissue. Such subjects include but are not limited to those afflicted with Alzheimer's Disease, Parkinson's Disease, peripheral nerve injury, peripheral neuropathy, amyotrophic lateral sclerosis, head injury, and stroke. The present invention is particularly useful in treating Alzheimer's Disease.

Subjects suitable for carrying out the present invention are, in general, mammals and avians, including but not limited to humans, monkeys, equines, caprines, bovines, ovines, porcines, dogs, cats, rabbits, rats, hamsters, mice, quail, chickens and turkeys. Human subjects are presently preferred for in vivo administration. Similarly, cultured neural tissues/cells for use with the inventive methods include mammalian and avian tissues and cells, including but not limited to neural tissues and cells derived from humans, monkeys, equines, caprines, bovines, ovines, porcines, dogs, cats, rabbits, rats, hamsters, mice, quail, chickens and turkeys.

In the manufacture of a medicament according to the present invention, hereinafter referred to as a pharmaceutical formulation, the inventive compositions are typically admixed with a pharmaceutically acceptable carrier. For injection, the carrier will typically be a liquid. For other methods of administration, the carrier may be either solid or liquid, such as sterile, pyrogen-free water or sterile pyrogen-free phosphate-buffered saline solution.

For the preparation of these compositions for administration to a subject, use can be made of pharmaceutical carriers adapted for conventional forms of administration, for example, injection solutions, tablets, capsules, dragees, syrups, solutions, suspension and the like. As an injection medium, it is preferred to use water which contains the additives usual in the case of injection solutions, such as stabilizing agents, salts or saline, and/or buffers. The active agent or its pharmaceutical formulation may be contained within a nutritional medium, e.g., in nutritional supplements. Oral formulations may be slow release preparations or enteric coated preparations to facilitate delivery of the peptide to the small intestine.

When administering apoE:CNTF complexes to a subject in need thereof, any suitable route of administration may be employed, including administration by parenteral injection (e.g., subcutaneous, intramuscular, or intradermal), or by oral, rectal, topical, nasal, ophthalmic, intrathecal, and intracerebral administration.

The apoE:CNTF complexes are included in an amount effective to accomplish the intended treatment. In general, the apoE:CNTF complexes are present in an amount effective to enhance survival of neural cells. ApoE:CNTF complexes may be administered concurrently or in combination with other agents.

The precise amount of an apoE:CNTF complex to be administered is determined in a routine manner, and will vary depending on the age and species of subject, the desired effect, the apoE isoform, and the route of administration. Preferred dosages may be determined by simply administering a composition containing a known amount of apoE:CNTF complexes in vitro or in vivo to a subject, and monitoring the cells, tissue or subject for the desired effect, as would be known by one skilled in the art.

There are no particular upper or lower limits to the dosage of apoE:CNTF complexes to be administered according to the present invention. For in vivo administration dosages can be as low as 10, 3, 1, 0.5 or 0.1: g/kg body weight, or less. In vivo dosages can be as high as 10, 30, 50 or 100: g/kg body weight, or more. In general, the in vivo dosage of apoE:CNTF complexes administered will be sufficient to result in peak plasma concentration of the complex of from about $1\times10^{-1}$, $1\times10^{0}$ or $1\times10^{1}$ picomole per Liter to about $1\times10^{2}$, $1\times10^{3}$ or even $1\times10^{4}$ picomole per Liter or more.

Similarly, there are no particular lower or upper limits to the dosages of the claimed complexes to be administered in vitro. For in vitro administration dosages can be as low as 5, 1, 0.5, 0.1 or 0.01 ng/ml of medium, or less. In vitro dosages can be as high as 5, 10, 30, 50 or 100 ng/ml of medium, or more.

The following Examples are provided to illustrate the present invention, and should not be construed as limiting thereof.

Example 1

ApoE/CNTF Gel-Shift Assays

Delipidated apoE was purified from individuals homozygous for apoE3 or apoE4, as previously described (Rall et al., (1986) *Methods Enzymol.* 128, 273). ApoE3 or apoE4 were incubated with recombinant human CNTF (generously provided by Regeneron Pharmaceuticals, Tarrytown, N.Y.) in Tris-buffered saline (TBS; see figure legends for specifics on quantities of proteins) for up to 4 hours at 37° C. ApoE was also incubated with control growth factors: LIF, a member of the four-helix bundle family of growth factors; NT3, a member of the neurotrophin family; and the fibroblast growth factor bFGF (LIF: R&D Systems, Minneapolis, Minn.; NT3: Regeneron Pharmaceuticals; bFGF: Collaborative Biomedical Products, Bedford, Mass.). Incubations were terminated by adding 4× SDS-Laemmli buffer without reducing agents. Proteins were electrophoretically separated by SDS-PAGE (see figures for percentage of polyacrylamide gels), and transferred to PVDF membrane (Immobilon P, Millipore, Bedford, Mass.). The membranes were blocked in Blotto (5% dried milk in TBS, pH 7.6, with 0.05% Tween [Surfact Amps-20, Pierce, Rockford, Ill.]) for one hour then incubated in primary antibody for one hour. The anti-apoE antibody was a polyclonal goat anti-human apoE (Calbiochem, San Diego, Calif.) diluted 1:2000 in Blotto. The anti-human CNTF antibody was a monoclonal antibody (R&D Systems) diluted 1:2000 in Blotto. Membranes were washed in Blotto three times, ten minutes each wash, then incubated with the secondary antibody for one hour. All incubations and washes were done at 25° C. For detecting the anti-apoE antibody, the secondary antibody was a swine anti-goat IgG conjugated to horseradish peroxidase (HRP; Boehringer Mannheim Biochemicals, Indianapolis, Ind.) diluted 1:3000 in Blotto. The secondary antibody for the anti-CNTF antibody was an HRP-conjugated goat anti-mouse IgG F(ab) (Boehringer Mannheim Biochemicals) diluted 1:1500 in Blotto. The enzyme-conjugated antibodies were visualized by addition of ECL chemiluminescent substrate (Amersham, Arlington Heights, Ill.) and exposure to Hyperfilm (Amersham) as previously described (Strittmatter et al., (1993) *Proc. Nat. Acad. Sci. USA* 90, 1977).

To determine whether apoE in human CSF forms a complex with CNTF, 500 ng of CNTF were added to 10 µl of human CSF. CSF samples were collected by diagnostic lumbar puncture after informed consent. Eight samples of CSF that had been previously genotyped for apoE isoform and stored at –80° C. were used. In addition, two freshly collected samples of CSF, stored at 4° C., were tested. The genotype of these latter two samples was not determined, but the apoE dinner on non-reduced gels indicated the presence of at least one APOE3 or APOE2 allele. Samples were processed and immunoblots run as described above.

Example 2

Substrate-Capture Immunoblot (SCIB) Assay

Three hundred ng of apoE3 or apoE4 in 20 µl TBS were incubated in polypropylene tubes (Eppendorf) for one hour, then unbound apoE was washed away with five changes of TBS. ApoE coated and control tubes were then blocked with 100 µl of 2% BSA (Sigma, St Louis, Mo.) for one hour and washed five times with TBS. CNTF (300 ng in 20 µl of Tris-1M NaCl) was incubated in ApoE coated tubes and in control tubes for two hours at 37° C. Unbound CNTF was removed with five washes of Tris-1M NaCl. After a final wash with TBS, 4× non-reducing Laemnili buffer was added to remove bound proteins from the tubes. Proteins were separated on 10% polyacrylamide gels (precast gels from Bio-Rad, Hercules, Calif.), transferred, blocked and probed with anti-CNTF antibody as described above.

To strip the membranes for reprobing with anti-ApoE antibody the proteins were fixed to the PVDF membrane with 50% methanol/10% acetic acid before blocking with Blotto. After probing the membranes with anti-CNTF antibody, the membranes were stripped in 200 mM glycine-HCL with 0.05% Tween, pH 2.5, at 80° C. for one hour. Membranes were processed in ECL and exposed to film to insure that there was no residual signal from the HRP-conjugated secondary antibody. The membranes were then blocked and probed with anti-ApoE antibody as described above.

Example 3

Eippocampal Bioassays—Substrates for Cell Culture

Ninety-six-well plates were coated with 100 µl of 10 µg/ml poly-D-lysine (PDL) for three hours at room temperature. Wells were washed with sterile water three times, then plated with 100 µl of 10 µg/ml laminin diluted in Hank's balanced salt solution (HBSS; Gibco, Gaithersburg, Md.) and incubated overnight at 37° C. On the morning of culture, the plates were washed three times with Opti-MEM (Gibco). ApoE3 or apoE4 were prepared in Opti-MEM at a concentration of 1 ng/ml, and 100 µl/well was incubated in the PDL/laminin coated wells at 37° C. After three hours, the wells were washed with three changes of Opti-MEM to remove unbound apoE. Serial dilutions of CNTF (0.004–25 ng/ml in Opti-MEM) were added to the plates three hours before the cells were dissociated, then 100 µl of cell suspension was added to the wells, bringing the final volume of media to 200 µl/well.

Example 4

Preparation and Plating of Rat Embryonic Hippocampal Neurons

Dissociated hippocampal neurons were prepared using a modification of a previously described method (Banker and Cowen, (1977) *Brain Res.* 126, 397); Goslin and Banker, Rat Hippocampal Neurons in Low-Density Culture, in NERVE CELLS (Banker and Goslin, eds. 1991). Hippocampi were dissected from embryonic day 18 rats. To minimize the number of contaminating astrocytes, the hippocampus was carefully dissected to avoid the overlying cortex. The meninges were removed and the cells incubated in $Ca^{++}$, $Mg^{++}$-free HBSS (Gibco) with 0.005% (w/v) trypsin at 37° C. for 15 minutes. The cells were washed and triturated in DMEM/F12 medium (Gibco) with 10% fetal calf serum (Gibco). The cells were pelleted by centrifugation and resuspended in Opti-MEM medium with 1% N2 supplement (Gibco). Cells were counted and resuspended to a final concentration of $5 \times 10^6$ cells/ml and plated at an initial density of 50,000 cells/well. AlbuMAX I (Gibco) was added as a supplement at a final concentration of 2 mg/ml. Cells were cultured for 72 hours at 37° C. in 5% CO2.

Images of the hippocampal cultures were collected after 72 hours in vitro by viewing the cultures under phase though a 32× objective on a Zeiss inverted microscope. Cultures were photographed using Kodak TMAX film.

Example 5

MTS Survival Assay

Viability was assayed after 72 hours in vitro using the Promega viability assay (CellTiter 96 AQueous, Promega, Madison, Wis.). See Ip and Yancopoulos, (1992) *Progress in Growth Factor Res.* 4, 1; Riddle et al., (1995) *Nature* 378, 189. This is a colometric assay in which the tetrazolium compound (3-(4,5-dimethylthiazo-2-yl)-5-(3-carboxymethoxyphenyl)-2-(4-sulfophenyl)2H-trazolium (MTS) is reduced by viable cells into a soluble formazan product. The absorbance of the formazan is measured directly from the 96 well plates. The quantity of formazan product as measured by absorbance at 490 nm is proportional to the number of viable cells. For performing this assay, 100 µl of media were removed from each well before adding 20 µl of MTS solution to each well. Plates were returned to the incubator and absorbance read by a Dynatech MR5000 microplate reader (Dynatech Laboratories) after a four hour incubation. The data were collected and calculated as the percent difference between each treatment group and the matched control (no apoE/no CNTF condition) for each experiment. The value for the no apoE/no CNTF condition was set at 100%. The percent differences for the separate experiments were then averaged.

Example 6

ApoE Binds to CNTF

Substrate-capture immunoblot (SCIB) assay was used to test whether CNTF binds apoE. This SCIB assay took advantage of the fact that apoE readily absorbs to plastic surfaces, presumably because of hydrophobic interactions. Purified, renatured, lipid-free apoE3 or apoE4 isolated from human serum were bound to microfuge tubes, blocked with BSA, then incubated with recombinant human CNTF. As a control for non-specific binding of CNTF, we incubated CNTF in a BSA-blocked tube, without apoE. After washing away unbound CNTF with 1 M NaCl-Tris, we stripped the retained proteins by adding non-reducing Laemmli buffer and separated the proteins by SDS-PAGE. Western blots were probed with an anti-CNTF antibody, then stripped and reprobed with an anti-apoE antibody. CNTF was retained when apoE3 or apoE4 were first bound to the tube. Both CNTF monomer and homodimer were retained by apoE. In contrast, there was essentially no binding of CNTF to the BSA-blocked surface: only a trace amount of CNTF homodimer was detected from the BSA blocked control tube. These data demonstrate that both isoforms of ApoE bind CNTF monomer and dimer even at high salt concentrations.

Example 7

ApoE3 Forms an SDS-Stable Complex with CNTF

We have characterized a number of apoE-protein interactions (e.g. tau, ∃-amyloid and laminin; reviewed by Strittmatter and Roses, (1995) *Proc. Nat. Acad. Sci. USA* 92, 4725) that are stable in ionic detergent. Because of the structural homology between CNTF and the amino terminal domain of ApoE, and since apoE3 and CNTF each form SDS-stable homodimers, we tested whether apoE and CNTF can form an SDS-stable heterocomplex. We incubated purified apoE3 or apoE4 with recombinant human CNTF in solution. Incubating apoE3 with CNTF produced a new protein species detected by SDS-PAGE with an apparent molecular weight consistent with a bimolecular apoE3/CNTF complex (molecular mass of apoE is 34 kd and of CNTF is 24 kd). This species was not seen with apoE3, apoE4 or CNTF alone. Incubating apoE4 with CNTF did not produce this new species.

More rigorous proof that apoE3 forms a molecular complex with CNTF was obtained by showing that the presumptive apoE complex is immunoreactive with both CNTF and apoE antibodies. Western blots were probed with anti-apoE and anti-CNTF antibodies, and the presumed apoE3/CNTF complex was immunoreactive for both anti-apoE and anti-CNTF antibodies. The apoE3/CNTF complex could be detected within thirty minutes of incubation and reached a maximum at 3–4 hours. Binding of apoE3 to CNTF is inhibited by the cysteine-reducing agent TCEP (tris(2-carboxyethyl)phosphine; Han and Han, (1994) *Anal. Biochem.* 220, 5; Gray, (1993) *Protein Sci.* 2, 1732), and the apoE3/CNTF complex dissociates in Laemmli buffer containing the reducing agent β-mercaptoethanol (β-ME), strongly suggesting that the apoE3/CNTF complex is disulfide-linked. ApoE4, which has no cysteine residues, does not form an SDS-stable complex with any of these growth factors.

Complex formation between proteins can be an artifact produced by boiling in non-reducing Laemmli buffer (Kumar and Davidson, (1992) *Biotechniques* 12, 198). Two experiments indicated that the apoE3/CNTF complex was produced during incubation and not during boiling. First, complex formation was observed whether or not the proteins were boiled in non-reducing Laemmli buffer. Second, the amount of complex formed was dependent on the incubation time, and not on whether the samples were boiled or on the duration of boiling.

Additional support for our model that apoE3 forms a disulfide bond with CNTF comes from determining which domain of apoE binds to CNTF. Thrombin cleaves apoE to produce two fragments; a 22 kD amino-terminus fragment containing the hydrophilic, receptor-binding region and a 10 kD carboxy-terminus fragment containing the hydrophobic, lipid-binding region (reviewed by Weisgraber, (1994) *Adv. Protein Chem.* 45, 249). It was determined that CNTF binds the 22 kD amino terminus fragment of apoE3 that contains the single cysteine of apoE3. This 22 kD fragment of apoE shares the four helix structure with CNTF.

Example 8

ApoE3 in Human Cerebrospinal Fluid (CSF) Forms a Complex with CNTF

As demonstrated above, purified, serum-derived apoE can bind CNTF. To assure ourselves that native apoE (rather than only purified, delipidated apoE) can bind CNTF, we tested samples of cerebral spinal fluid (CSF) from APOE3/3 and APOE4/4 individuals for their ability to form an apoE/CNTF complex. In addition, we wanted to determine whether native apoE in CSF binds to CNTF, even in the presence of other proteins. The SCIB assay described above (Example 2) is not appropriate for this experiment: if the mixture of proteins in CSF were absorbed to a microfuge tube we could not determine whether CNTF bound apoE or some other CSF protein. However, since the apoE3/CNTF complex can be identified by SDS-PAGE, we could determine whether apoE in CSF binds CNTF under this assay condition. CSF samples from five APOE3/3 individuals and from three APOE4/4 individuals were tested for their ability to produce an apoE/CNTF complex. All samples of CSF from APOE3 homozygous individuals produced an apoE/CNTF complex with exogenous CNTF. The apoE monomer is sometimes resolved as a doublet at approximately 34 kd, due to differences in post-translational sialation of apoE (Zannis et al., (1984) *J. Biol. Chem.* 259, 5495. In many of our gels, the apoE3/CNTF complex was resolved as a doublet suggesting that CNTF binds both sialyated and non-sialyated apoE3. No CSF samples from APOE4/4 individuals formed an SDS-stable apoE4/CNTF complex.

Since the CSF samples described above had been stored frozen, (freezing can denature lipoprotein particles), we tested whether apoE in fresh CSF, and therefore lipid-bound, would form a complex with CNTF. Two samples of freshly collected CSF were incubated with CNTF and probed for the presence of an apoE/CNTF complex. In both cases we observed complex formation that was indistinguishable from the complex generated in the frozen samples, indicating that apoE in a lipid particle can bind CNTF. These results support the conclusion that apoE3 and not apoE4 forms an SDS-stable apoE/CNTF complex. Most importantly, however, we have demonstrated that native apoE3 binds CNTF, even in the presence of the mixture of proteins in CSF.

Example 9

Effects of ApoE on Biologic Activity of CNTF in vitro

Having found that both apoE3 and apoE4 can bind CNTF and that this binding occurs between native apoE and CNTF, we asked whether apoE alters the biologic activity of CNTF. To assess the effect of apoE on the biologic activity of CNTF we assayed survival of cultured embryonic rat hippocampal neurons.

Survival of embryonic day 18 (E18) rat hippocampal neurons is supported by CNTF. Ip et al., (1991) *J. Neurosci.* 11, 3124. However, these and other studies examining CNTF activity have included fetal bovine serum either during the initial plating of cells or throughout the experiments. Hughes et al., (1988) *Nature* 335, 70; Ernsberger et al., (1989) *Neuron* 2, 1275; Saadat et al., (1989) *J. Cell. Biol.* 108, 1807; Arakawa et al., (1990) *J. Neurosci.* 10, 3507; Magal et al., (1991) *Brain Res. Dev. Brain Res.* 63, 141; Ip et al., (1992) *Cell* 69, 1121; Unsicker et al., (1992) *Brain Res. Dev. Brain Res.* 65, 285; Magal et al., (1993) *Dev. Neurosci.* 4, 779. Because serum contains apoE, (approximately 30 μg/ml), we used a protocol that does not require serum during the initial plating of the hippocampal neurons or during culture (Examples 3 & 4).

Figure 1:
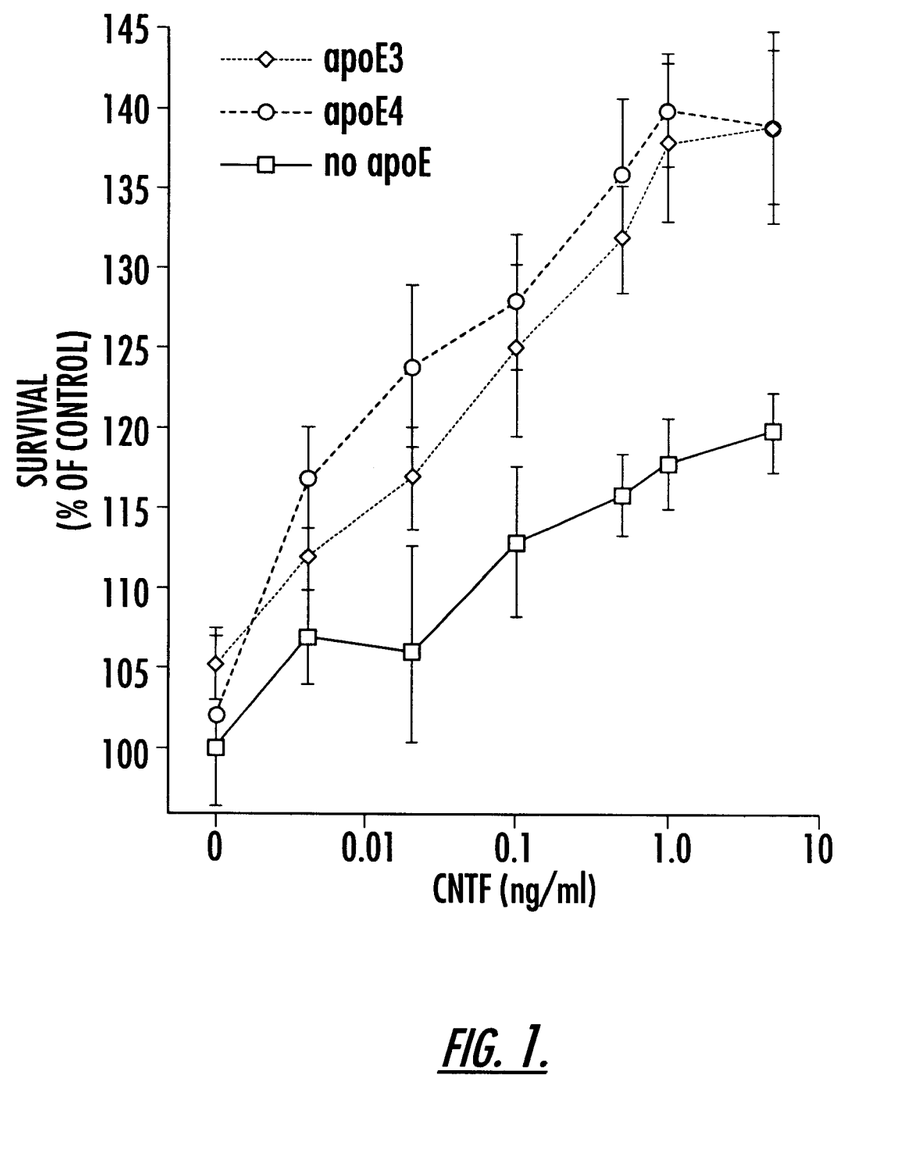
FIG. 1 shows the dose-response effect of CNTF on survival of hippocampal neurons in the presence of either apoE3 or apoE4. The 96-well plates were preplated with 1 ng/ml of apoE3 or apoE4. Control plates had no apoE. Dissociated hippocampal cells were cultured in the presence or absence of increasing concentrations of CNTF (0.004–25 ng/ml) for 3 days. Survival was assayed at the end of the culture period by the MTS viability assay. The results from four independent experiments were compared with controls ∀ SEM (n=4–5/experiment). The difference in maximum survival between apoE and no apoE conditions is significant at $p<0.0005$, using the Student's t test for the differences between the means.

Neither apoE3 nor apoE4 alone significantly increased survival of hippocampal cells over control values (the absorbance value of the "no apoE/no CNTF" condition was the control value, and all data within each experiment were normalized to the control values of that experiment). However, both apoE3 and apoE4 significantly enhanced the survival promoting activity of CNTF for E18 hippocampal cells. In the absence of apoE, 1 ng/ml CNTF promoted survival at a maximum of 20±2.5% over control survival (mean±SEM, average of four experiments, n=4–5/experiment) (FIG. 1). Even at much higher concentrations of CNTF (25 ng/μl) there was no further increase in hippocampal neuron survival (survival at 25 ng/ml CNTF was 18±4% over control). However, when apoE was bound to the plates prior to addition of CNTF, survival of hippocampal neurons was significantly increased. With apoE, CNTF promoted the survival of the hippocampal cultures in a dose dependent manner: in the presence of apoE3 and apoE4, CNTF produced maximum survival of 39±4.8% and 40±3.5% over controls, respectively (the difference in maximum survival between the "apoE" and "no apoE" conditions was significant at p<0.0005). In the presence and absence of apoE maximum survival was obtained at a CNTF concentration of approximately 1 ng/ml.

Surviving cells in all conditions had a healthy, phase-bright appearance, and extended long, branching neurites. Where isolated neurons were seen, there were no apparent differences in neuronal morphologies observed under the different culture conditions, although no detailed analysis of morphology was performed.

As a control, we tested whether MTS absorbance values were equivalent across the different culture conditions at four hours after plating the hippocampal cultures. MTS absorbance was tested in the presence and absence of 1 ng/ml apoE3 for the following CNTF concentrations: 0 ng/ml CNTF; 1 ng/ml CNTF and; 5 ng/ml CNTF. For the no apoE3 condition, MTS values at the tested CNTF concentrations were: 0 ng/ml CNTF=0.351±0.002; 1 ng/ml CNTF= 0.356±0.006; 5 ng/ml CNTF=0.359±0.007. For the 1 ng/ml apoE3 condition the MTS absorbance values were: 0 ng/ml CNTF=0.353±0.003; 1 ng/ml CNTF=0.353 0.01; 5 ng/ml CNTF=0.35±0.01. There were no significant differences among these conditions, indicating that differences in initial plating density did not account for differences in survival seen at 72 hours.

This bioassay result is significant because it demonstrates a functional consequence of apoE binding to CNTF. Because both apoE and CNTF are expressed locally after CNS injury, it is quite plausible that apoE promotes the neuronal survival promoting activity of CNTF in vivo. Since apoE3 preferentially promotes recovery from trauma in vivo, it is likely that in certain environments apoE3 promotes CNTF function better than apoE4 because apoE3 can form a disulfide bond with CNTF.

Example 10

ApoE Protects Complexed CNTF from Proteolytic Degradation

Both apoE and CNTF accumulate at sites of injury, where a variety of proteases are active. It was known that apoE is hydrolyzed by the proteolytic activity of the serine protease 7S NGF. 7S NGF contains the gamma NGF subunit, a serine protease that cleaves substrates at arginine residues. (Thrombin, another serine protease with similar substrate specificity, produces the two domains of apoE). Recombinant 2.5S NGF, which lacks the gamma subunit, does not proteolyze apoE3.

Studies were carried out to evaluate the rate of proteolytic degradation of the apoE3/CNTF complex. One microgram of apoE3, 1 μg CNTF, or 0.5 μg apoE3+0.5 μg CNTF were incubated in TBS for 3 hours at 37° C. Fifty nanograms of 7S NGF was used to proteolyze each sample for time periods up to 3 hours. Samples were separated under nonreducing conditions and blotted with either anti-CNTF or anti-apoE.

It was observed that both CNTF and apoE3 are readily degraded by 7S NGF, but both are protected against proteolysis if first allowed to form an apoE3/CNTF complex. Because there is no change in molecular weight following incubation with 7S NGF, apoE3 and CNTF appear to protect each other from this protease. The apoE3/CNTF complex is resistant to proteolysis even after incubation for six hours with 7S NGF added every two hours. These results suggest that apoE potentiates CNTF activity by protecting CNTF from proteases secreted at sites of injury.

All publications and patent applications mentioned in the specification are indicative of the level of those skilled in the art to which this invention pertains.

Although the foregoing invention has been described in some detail by way of illustration and example for purposes of clarity and understanding, it will be obvious that certain changes and modifications may be practiced within the scope of the appended claims.

That which is claimed is:

1. A composition comprising an isolated complex of apolipoprotein E and ciliary neurotrophic factor, wherein said complex enhances neural cell survival in vitro.

2. A composition according to claim 1, wherein said apolipoprotein E is a delipidated apolipoprotein E.

3. A composition according to claim 1, wherein said apolipoprotein E is lipid-bound.

4. A composition according to claim 1, wherein said complex is a covalent complex.

5. A composition according to claim 1, wherein said complex is bound to a substrate.

6. A composition according to claim 1, wherein said apolipoprotein E is apolipoprotein E2.

7. A composition according to claim 1, wherein said apolipoprotein E is apolipoprotein E3.

8. A composition according to claim 1, wherein said apolipoprotein E is apolipoprotein E4.

9. A composition according to claim 1, wherein said apolipoprotein E is human apolipoprotein E.

10. A composition according to claim 1, wherein said ciliary neurotrophic factor is human ciliary neurotrophic factor.

11. A method of enhancing the survival of neural cells, comprising administering to neural cells in vitro a survival enhancing amount of a composition comprising the isolated complex of apolipoprotein E and ciliary neurotrophic factor for a time and under conditions to enhance the survival of neural cells.

12. A method according to claim 11, wherein the apolipoprotein E is a delipidated apolipoprotein E.

13. A method according to claim 11, wherein the apolipoprotein E is lipid-bound.

14. A method according to claim 11, wherein the complex is a covalent complex.

15. A method according to claim 11, wherein the apolipoprotein E is apolipoprotein E2.

16. A method according to claim 11, wherein the apolipoprotein E is apolipoprotein E3.

17. A method according to claim 11, wherein the apolipoprotein E is apolipoprotein E4.

18. A method according to claim 11, wherein the apolipoprotein E is human apolipoprotein E.

19. A method according to claim 11, wherein the ciliary neurotrophic factor is human ciliary neurotrophic factor.

20. A method according to claim 19, wherein the complex is bound to a substrate.

21. A method according to claim 20, wherein the apolipoprotein E is bound to the substrate before forming the complex with the ciliary neurotrophic factor.

22. A composition comprising an isolated noncovalent complex of apolipoprotein E and ciliary neurotrophic factor.

23. A composition comprising an isolated covalent complex of apolipoprotein E and ciliary neurotrophic factor, wherein said covalent complex is a disulfide bonded complex between the apolipoprotein E and the ciliary neurotrophic factor molecules.

24. A composition comprising an isolated complex of apolipoprotein E and ciliary neurotrophic factor produced by combining together a composition containing apolipoprotein E and a composition containing ciliary neurotrophic factor.

25. A method of enhancing the survival of neural cells, comprising administering to neural cells in vitro a survival enhancing amount of a composition comprising the isolated noncovelant complex of apolipoprotein E and ciliary neurotrophic factor for a time and under conditions to enhance the survival of neural cells.

26. A method of enhancing the survival of neural cells, comprising administering to neural cells in vitro a survival enhancing amount of a composition comprising the isolated covalent complex of apolipoprotein E and ciliary neurotrophic factor, wherein said covalent complex is a disulfide bonded complex, for a time and under conditions to enhance the survival of neural cells.

27. A method of enhancing the survival of neural cells, comprising administering to neural cells in vitro a survival enhancing amount of a composition comprising the isolated complex of apolipoprotein E and ciliary neurotrophic factor, wherein the complex is produced by combining together a composition containing apolipoprotein E and a composition containing ciliary neurotrophic factor, for a time and under conditions to enhance the survival of neural cells.

* * * * *

UNITED STATES PATENT AND TRADEMARK OFFICE
CERTIFICATE OF CORRECTION

PATENT NO. : 6,313,089 B1  Page 1 of 1
APPLICATION NO. : 09/135905
DATED : November 6, 2001
INVENTOR(S) : Matthew et al.

It is certified that error appears in the above-identified patent and that said Letters Patent is hereby corrected as shown below:

IN THE CLAIMS

Column 14, line 37 should read as follows:

▪ 20. A method according to claim 11, wherein the complex ▪

Column 14, line 39 should read as follows:

▪ 21. A method according to claim 24, wherein the apoli- ▪

Signed and Sealed this

Nineteenth Day of February, 2008

JON W. DUDAS
*Director of the United States Patent and Trademark Office*